(12) United States Patent
Pehr et al.

(10) Patent No.: US 12,275,224 B2
(45) Date of Patent: Apr. 15, 2025

(54) WOUND CLEANING PRODUCT

(71) Applicant: CARL FREUDENBERG KG, Weinheim (DE)

(72) Inventors: Marc Pehr, Laudenbach (DE); Birthe Lang, Weinheim (DE); Bernd Schlesselmann, Weinheim (DE)

(73) Assignee: CARL FREUDENBERG KG, Weinheim (DE)

( * ) Notice: Subject to any disclaimer, the term of this patent is extended or adjusted under 35 U.S.C. 154(b) by 402 days.

(21) Appl. No.: 17/630,938

(22) PCT Filed: Jul. 10, 2020

(86) PCT No.: PCT/EP2020/069478
§ 371 (c)(1),
(2) Date: Jan. 28, 2022

(87) PCT Pub. No.: WO2021/018544
PCT Pub. Date: Feb. 4, 2021

(65) Prior Publication Data
US 2022/0203650 A1    Jun. 30, 2022

(30) Foreign Application Priority Data

Jul. 31, 2019   (DE) ............... 10 2019 120 712.6

(51) Int. Cl.
| | |
|---|---|
| *B32B 5/24* | (2006.01) |
| *B32B 5/06* | (2006.01) |
| *B32B 5/18* | (2006.01) |
| *D04H 1/498* | (2012.01) |

(52) U.S. Cl.
CPC ............ *B32B 5/245* (2013.01); *B32B 5/06* (2013.01); *B32B 5/18* (2013.01); *D04H 1/498* (2013.01);

(Continued)

(58) Field of Classification Search
CPC .. B32B 5/06; B32B 5/245; B32B 5/18; B32B 2250/02; B32B 2260/021; B32B 2266/06;
(Continued)

(56) References Cited

U.S. PATENT DOCUMENTS

| | | |
|---|---|---|
| 3,122,141 A | 2/1964 | Crowe, Jr. |
| 3,156,242 A | 11/1964 | Crowe, Jr. |

(Continued)

FOREIGN PATENT DOCUMENTS

| | | |
|---|---|---|
| CA | 734221 A | 5/1966 |
| CH | 410296 A | 3/1966 |

(Continued)

OTHER PUBLICATIONS

Translation of WO2017032778A1 (abstract, description and claims) (Year: 2017).*

*Primary Examiner* — Catherine A. Simone
(74) *Attorney, Agent, or Firm* — LEYDIG, VOIT & MAYER, LTD.

(57) ABSTRACT

A wound cleaning product is described as used for sterile debridement of wounds. The wound cleaning product comprises a composite material having a foam layer and a fiber layer arranged on a surface of the foam layer. The fiber layer is at least partially thermally solidified, and the foam layer and the fiber layer are connected to one another by needling such that fibers of the fiber layer have penetrated into the foam layer and form capillary channels that extend from the fiber layer into the foam layer.

14 Claims, 6 Drawing Sheets

(52) U.S. Cl.
CPC ..... *B32B 2250/02* (2013.01); *B32B 2260/021* (2013.01); *B32B 2266/06* (2013.01); *B32B 2307/54* (2013.01); *B32B 2307/728* (2013.01); *B32B 2307/73* (2013.01); *B32B 2535/00* (2013.01)

(58) Field of Classification Search
CPC ............ B32B 2307/54; B32B 2307/73; B32B 2307/728; B32B 2535/00; D04H 1/498
See application file for complete search history.

(56) References Cited

U.S. PATENT DOCUMENTS

| | | | |
|---|---|---|---|
| 3,301,257 A | 1/1967 | Crowe, Jr. | |
| 4,360,015 A | 11/1982 | Mayer | |
| 4,731,277 A | 3/1988 | Groitzsch et al. | |
| 10,238,550 B2 | 3/2019 | Engl et al. | |
| 2003/0079324 A1 | 5/2003 | Collins et al. | |
| 2006/0135026 A1 | 6/2006 | Arendt et al. | |
| 2017/0304485 A1 | 10/2017 | Kshirsagar | |

FOREIGN PATENT DOCUMENTS

| | | | | |
|---|---|---|---|---|
| DE | 202015103600 U1 | 10/2016 | | |
| EP | 0211131 A2 | 2/1987 | | |
| EP | 2365794 B1 | 3/2013 | | |
| EP | 2777662 B1 | 7/2015 | | |
| GB | 2464970 A | 5/2010 | | |
| WO | WO 2013113906 A1 | 8/2013 | | |
| WO | WO-2017032778 A1 | * 3/2017 | ............ | A47L 13/16 |
| WO | WO 2019028057 A1 | 2/2019 | | |
| WO | WO 2019057256 A1 | 3/2019 | | |

* cited by examiner

WOUND CLEANING PRODUCT

CROSS-REFERENCE TO PRIOR APPLICATIONS

This application is a U.S. National Phase application under 35 U.S.C. § 371 of International Application No. PCT/EP2020/069478, filed on Jul. 10, 2020, and claims benefit to German Patent Application No. DE 10 2019 120 712.6, filed on Jul. 31, 2019. The International Application was published in German on Feb. 4, 2021 as WO 2021/018544 under PCT Article 21(2).

FIELD

The invention relates to a wound cleaning product comprising a composite material having a foam layer and a fiber layer arranged on and in the foam layer, and to a method for its production.

BACKGROUND

In wound treatment, wound cleaning (debridement), i.e., the removal of necrotic (dead), infected, or damaged tissue, fibrin coatings, wound exudate, and other impurities from the wound, plays an integral role. Necrotic tissue and/or a strong presence of bacteria can strongly impede the healing process of a wound. For this reason, it is medically advised to perform a debridement, in particular in the case of chronic wounds, between each change of dressing. There are various methods that are used for wound cleaning. When removing dead tissue, it is essential in all methods to not damage newly formed granulation and young epithelial tissues, which form upon wound closure.

One method that is increasingly being used is mechanical wound cleaning. Here, various fabrics, for example textiles or sponges, are used to clean the wound. An advantage of mechanical wound cleaning is that it is easy to carry out and can also be applied in home care by nursing staff.

The requirements for fabrics for mechanical wound cleaning are numerous. On the one hand, they must have an abrasive character that is matched to the application and allows gentle painless removal of necrotic tissue and of coatings, and on the other hand they must have good absorbency, which allows rapid absorption of the detached wound coatings and thus prevents re-contamination of the wound. In addition, the fabric should also be suitable for cleaning the surrounding skin, for which a less abrasive surface is suitable. Furthermore, the structure should be flexible so that a wide variety of wound geometries can be cleaned, i.e., both large-area wounds and tunneling wounds.

The use of various fabrics for mechanical wound cleaning is already known.

WO 2019/028057 A1 describes a hydrophilic foam with a moisture content between 20 wt. % and 60 wt. % with a structure that allows for debriding the wound. The disadvantage here is that abrasiveness is determined by the moisture content. This is not practical in use since it is very difficult for the nursing staff to use the wound irrigation solution in a metered manner. Another disadvantage is that surfaces with different abrasiveness are not available for cleaning.

WO 2019/057256 A1 discloses two foam layers that are joined by lamination. On the one side, there is a foam side with recesses and grooves. Various structures and surfaces for cleaning are provided. A disadvantage of this system is that the lamination of the two foams can lead to increased rigidity. Furthermore, different swelling behavior of the foams bears the risk of delamination of the layers.

A commercially available foam for mechanical debridement is the wound cleaning sponge Wundputzer® by Ligasano®. The reticulated hydrophobic foam exhibits good cleaning performance due to its strongly abrasive structure. However, this structure can also lead to severe pain in the patient during use. The reticulated foam has a high open porosity in order to remove solid and highly viscous wound components. However, this leads to reduced absorbency.

In addition to foams, the use of textile fabrics for wound cleaning is also described.

EP 2 365 794 B1 describes a wound cleaning device that has or is a cloth and that has a carrier layer with filaments, which project from or are arranged on said carrier and are made of synthetic fibers, which preferably have cut ends or end faces. The disadvantage is that the cleaning effect is achieved by the projecting fibers. This quickly results in adhesive bonding of the fiber ends, in particular in wounds with viscous exudate, which results in rapid exhaustion of the capacity of the cloth. In addition, due to their elongated geometry, the cavities provided between the fibers are not so well suited for absorbing and enclosing the wound components.

A commercially available product of the aforementioned structure is the wound cleaning product Debrisoft®. In addition to the aforementioned disadvantages, it is disadvantageous that the product has hard serged edges that can cause severe pain upon contact with the wound bed.

However, the edges are necessary to hold the textile structure together since fibers are released during cutting of the product and can lead to contamination of the wound. In addition, it is very rigid so that it is only suitable for use on flat wounds. Furthermore, exudate is bound only at the surface and is not absorbed within the structure of the cloth. Finally, it can be used only on one side.

EP 2777662 B1 describes a velour nonwoven for use in wound cleaning, characterized in that the fibers are present in loops. This is advantageous in that necroses and wound secretions can be easily removed due to the loop structure and can be absorbed within the structure. A disadvantage of the described invention is that abrasion and absorption are carried out by the same layer and, as a result, cannot be varied arbitrarily independently of one another.

US 20030079324 A1 describes a method for producing a structured permeable nonwoven, solidified by means of water jets, with high absorbency and good abrasion in particular when moist. The small thickness of the material caused by the production process is disadvantageous in this case, whereby only a small amount of space is available for absorbing and enclosing the wound components.

US 20170304485 A1 describes a particle-containing porous nonwoven matrix consisting of polyolefins and glass fibers, which contains a plurality of microorganism-binding particles. A disadvantage of using glass fibers is that they have a very high abrasiveness, which can be very unpleasant for the patient. Furthermore, various surfaces with different surface properties are not available.

A commercially available and widely used fiber-based mechanical wound cleaning product is cotton gauze. Cotton gauze is an open fabric made of cotton yarns and is characterized, on the one hand, by its favorable price and, on the other hand, by a high versatility. A disadvantage of this product is that it can be painful for the patient due to its coarse yarn structure. In addition, there is a risk of contamination of the wound by fiber components detaching from the yarn, in particular when cutting the gauze.

WO 2013/113906 A1 describes a wound care product having at least one surface with abrasive properties, which surface is designed such that the wound care product is suitable for breaking up biofilms arranged in the wound and/or inducing wound exudation when the product moves relative to a wound. The surface with abrasive properties may be a foam or fibers. Also described is a product containing both a polyurethane foam and textile material laminated thereon. A disadvantage of this composite material is its high rigidity and tendency to delamination. In addition, transport of wound exudate through the structure is made more difficult due to the lamination.

A commercially available product of the aforementioned structure is the wound cleaning product Cutimed® Debri-Clean. In addition to the aforementioned disadvantages, the product has the disadvantage that it has hard edges and a high rigidity, which makes it suitable only for large-area wounds. Furthermore, it can be used only on one side.

SUMMARY

In an embodiment, a wound cleaning product is provided for sterile debridement of wounds. The wound cleaning product comprises a composite material having a foam layer and a fiber layer arranged on a surface of the foam layer. The fiber layer is at least partially thermally solidified, and the foam layer and the fiber layer are connected to one another by needling such that fibers of the fiber layer have penetrated into the foam layer and form capillary channels that extend from the fiber layer into the foam layer.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
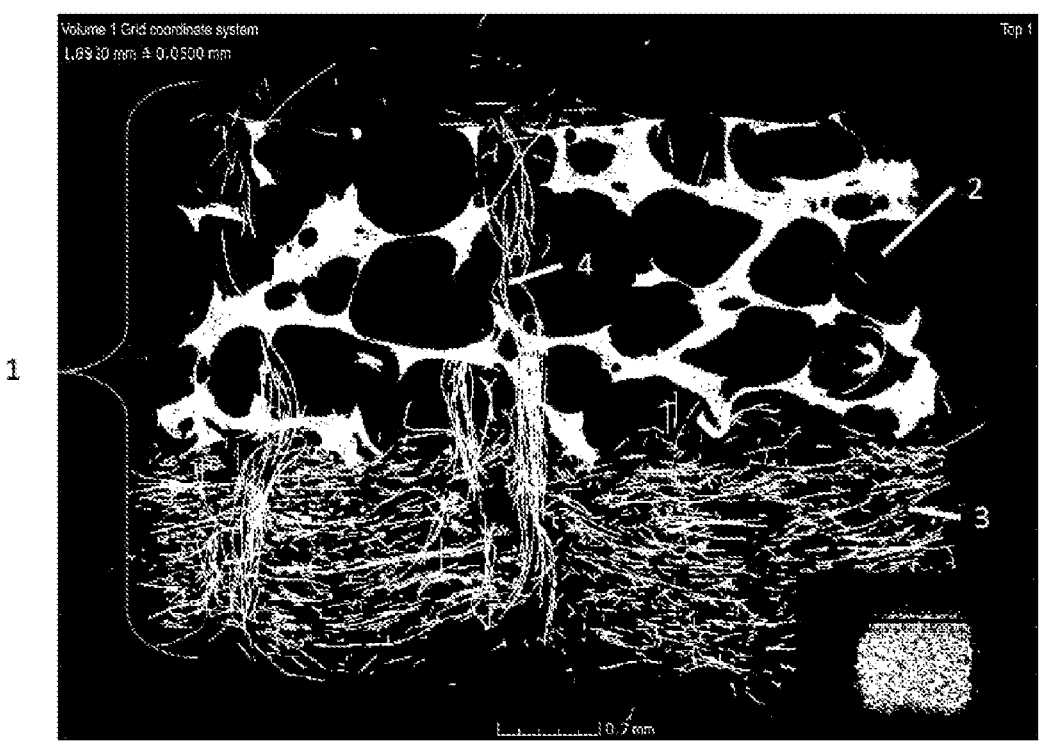
FIG. 1 shows the cross-section of a CT image of a composite material, according to an embodiment.

The object of the embodiments described herein is to provide a wound cleaning product with which the aforementioned disadvantages can be at least partially eliminated. In particular, the wound cleaning product is to enable good and gentle wound cleaning. In doing so, necrotic tissues and coatings should be able to be removed without the application of strong force so that the risk of damaging young granulation tissue is minimized. In addition, it should have at least two areas of different abrasiveness so that they can be optimized independently of one another for cleaning both the wound and the surrounding skin. This makes it possible to optimally treat both the wound and the surrounding skin with one product. The product should also be usable for various wound geometries, for example large-area or tunneling wounds. Furthermore, the product should be cuttable to size and usable without significant loss of fibers.

This object is achieved by a wound cleaning product comprising a composite material having a foam layer and a fiber layer arranged on and in the foam layer, wherein the fiber layer is at least partially thermally solidified, and wherein the foam layer and the fiber layer are connected to one another by needling, wherein fibers of the fiber layer have penetrated into the foam layer and form capillary channels that extend from the fiber layer into the foam layer.

The wound cleaning product according to an embodiment is characterized in that it has a foam layer and a fiber layer that are connected to one another by needling. As a result of this mechanical connection, fibers of the fiber layer penetrate into the foam layer and form capillary channels. Capillary channels are understood to mean the elongated cavities formed between the fibers aligned by the needling. The capillary channels extend from the fiber layer into the foam layer and thus enable a good and fast transport of exudate across layers and its enclosure in the entire wound cleaning product.

Needling the fiber layer and the foam layer produces a structure with high tensile strength. Thus, the composite material can have a maximum tensile strength/expansion measured according to EN 29073-03 (wet) of more than 40%, for example from 40% to 180%, preferably more than 50%, for example from 50% to 180%, more preferably more than 60%, for example from 60% to 180%, more preferably more than 70%, for example from 70% to 180%, more preferably more than 80%, for example from 80% to 180%, more preferably more than 90%, for example from 90% to 180%, and in particular more than 100%, for example from 100% to 180%. Furthermore, a double-sided material can be obtained in which there is no risk of delamination even in the event of swelling and the associated expansion of the layers.

Furthermore, it has surprisingly been found that the needling of the fiber layer and foam layer enables a liquid transport between the layers, which enables rapid removal of wound exudate and its secure enclosure inside the structure. In a preferred embodiment, the fibers of the fiber layer penetrate the foam layer and protrude at least partially from the side of the foam layer facing away from the fiber layer. This is advantageous as it can result in a particularly pleasant feel of the foam side. Moreover, the protruding fiber ends can even further increase the cleaning effect of the foam layer due to their high specific surface area.

In some applications, using the fiber layer instead of the foam layer as the cleaning side is advantageous since fibers are generally less abrasive than foams so that gentle cleaning of the surrounding skin is possible. In addition, the fibers offer a higher specific surface area than the foam for the cleaning and adsorption of small detached wound components and bacteria.

Furthermore, it has been found that the wound cleaning product enables gentle wound cleaning. In particular, viscous and crusted components can be detached even with slight pressure. Furthermore, the wound cleaning product enables various surface structures in a single material so that various cleaning needs can be addressed with a single product.

According to an embodiment, the fiber layer is thermally solidified. As a result of thermal solidification, the fibers can be easily fixed so that the risk of fiber loss and thus contamination of the wound can be reduced. In addition, the abrasiveness can be adjusted in a targeted manner via the degree of thermal solidification.

Thermal solidification preferably takes place in that the fiber layer is thermally solidified before being applied onto the foam layer. This makes it possible to prevent the foam layer from being impaired by the heating process.

In practical tests, it has been shown to be particularly expedient if the fiber layer is a fiber layer which has been thermally solidified without compression. This has the advantage that the pore volume is available to a great extent for absorbing wound components even after solidification. Furthermore, a fiber layer having a rough surface can thereby be obtained, which makes it possible to detach coatings in the wound that are hard to detach. In addition, this allows maintaining the flexibility of the fiber layer. Thermal solidification without compression can take place, for example, by treating the fiber layer with hot air, for example in a through-air furnace.

It is furthermore preferred if the fiber layer is an extensively thermally solidified fiber layer. This is advantageous in comparison to non-extensively thermally solidified fiber layers, such as point-calendered fiber layers, since individual fibers can thus be prevented from detaching from the fiber layer and contaminating the wound.

In a preferred embodiment, the fiber layer is a nonwoven, in particular a nonwoven according to DIN EN ISO 9092: 2019-08, a woven fabric, a stitch-bonded fabric and/or a knitted fabric, wherein the aforementioned fiber layers are each at least partially thermally solidified. The fiber layer is particularly preferably an at least partially thermally solidified nonwoven since, due to its open structure, it allows particularly good penetration of the fibers into the foam layer.

The fiber layer can have a wide variety of fibers. Synthetic fibers are preferred since they can be sterilized well. Also preferred are hydrophobic fibers, i.e., fibers that, at least at their surface, are made of polymers whose surface energy is less than 50 mJ/m$^2$. Particularly suitable hydrophobic fibers are polyester and/or polyolefin fibers. The advantage of hydrophobic fibers is that they allow the binding and thus the removal of bacteria. The binding of bacteria to hydrophobic fibers is described, for example, in N. Edwards et al., "Role of surface energy and nanoroughness in the removal efficiency of bacterial contamination by nonwoven wipes from frequently touched surfaces," Science and Technology of Advanced Materials, 2017, Vol. 18, No. 1, 197-209.

In order to form the framework structure, the fiber layer preferably has matrix fibers. Matrix fibers are to be understood as fibers that are not thermally fused or that are thermally fused only to a small extent. Preferred are thermoplastic matrix fibers that have a melting point of the lowest melting fiber component of greater than 170° C., for example from 170° C. to 250° C., more preferably greater than 200° C. In one embodiment, the matrix fibers consist of one fiber component. In a further preferred embodiment, the matrix fibers consist of a plurality of fiber components. Full profile fibers, multi-lobal full profile fibers, hollow fibers, and/or full profile bicomponent fibers (e.g., core-sheath, side-by-side) are particularly preferred. If the fiber layer has binding fibers, it is advantageous if the melting point of the fiber component with the lowest melting point contained in the matrix fiber is above the melting point of the fiber component with the highest melting point contained in the binding fiber. The melting point of the fiber component with the lowest melting point in the matrix fiber is preferably at least 10° C., particularly preferably at least 30° C., above the melting point of the fiber component with the highest melting point in the binding fiber. Suitable polymer classes for producing the matrix fibers may inter alia be polyesters, polyamides, polyolefins, polyacrylonitrile, cellulose, and/or polyvinyl alcohols.

Particularly suitable matrix fibers are hydrophobic matrix fibers.

The proportion of matrix fibers in the fiber layer is preferably at least 20 wt. %, for example from 20 wt. % to 90 wt. % and/or from 20 wt. % to 80 wt. %, and/or from 20 wt. % to 70 wt. %, more preferably at least 25 wt. %, for example from 25 wt. % to 80 wt. % and/or from 25 wt. % to 70 wt. %, more preferably at least 30 wt. %, for example from 30 wt. % to 70 wt. %, in each case in relation to the total weight of the fiber layer.

In a preferred embodiment, the fiber layer comprises a binder, for example thermoplastic binders and/or binding fibers. Binding fibers are fibers that are at least partially fused, thereby creating bonding points between the fibers. This allows thermal solidification and targeted adjustment of the abrasiveness of the fiber layer. Preferably, at least one fusible fiber component of the binding fiber, in particular an externally arranged fusible fiber component, has a melting point that is lower than the melting point of other fiber components contained in the fiber layer, in particular lower than the melting point of the lowest melting fiber component of the matrix fibers.

If the binding fiber has a plurality of fusible fiber components, the melting point of the highest melting fiber component of the binding fiber is preferably more than 10° C., particularly preferably more than 30° C., below the melting point of the lowest melting fiber component of the matrix fibers. Suitable binding fibers have a melting point of the highest melting fiber component of below 250° C., for example from 100° C. to 200° C., more preferably of below 180° C., for example from 100° C. to 180° C., in particular below 175° C., for example from 100° C. to 175° C.

Preferred fusible components in binding fibers are polyolefin, polyester, polyamide, and/or mixtures thereof, as well as copolymers, such as ethylene-vinyl acetate copolymers. Likewise preferred binding fibers are bicomponent fibers, in particular bicomponent fibers containing polyolefin, polyester, ethylene-vinyl acetate copolymers, polybutylene terephthalate, and/or mixtures thereof as the externally arranged fiber component. The binding fibers can have different cross-sectional geometries, such as full profile fiber, multi-lobal profile fiber, hollow fiber, or full profile bicomponent fiber (e.g., core-sheath, side-by-side) geometries. Fusible binding fibers in the form of full profile fibers are preferred.

Particularly suitable binders are hydrophobic binding fibers, in particular polyester and/or polyolefin fibers.

The proportion of binding fibers in the fiber layer is preferably at least 10 wt. %, for example from 10 wt. % to 80 wt. % and/or from 10 wt. % to 70 wt. %, and/or from 10 wt. % to 60 wt. %, more preferably at least 25 wt. %, for example from 25 wt. % to 80 wt. % and/or from 25 wt. % to 70 wt. %, and/or from 25 wt. % to 60 wt. %, more preferably at least 30 wt. %, for example from 30 wt. % to 80 wt. % and/or from 30 wt. % to 70 wt. %, and/or from 30 wt. % to 60 wt. %, in each case in relation to the total weight of the fiber layer.

Thermoplastic binders may be co-polyamide, co-polyesters, polyolefins, polyvinyl alcohol (PVA), ethylene-vinyl acetate (EVA), thermoplastic polyurethane (TPU), polycaprolactone, terpolymers, and/or mixtures thereof. The thermoplastic binder preferably contains the aforementioned polymers in an amount of more than 50 wt. %, particularly preferably of more than 70 wt. %, in particular more than 90 wt. %, in each case in relation to the total weight of the binder. Preferred thermoplastic binders have a melting point of 90° C. to 200° C. Particularly suitable thermoplastic binders are hydrophobic, i.e., made of polymers whose surface energy is less than 50 m J/m2.

In a preferred embodiment, the fibers contained in the fiber layer, in particular the matrix fibers and/or the binding fibers, are staple fibers, preferably with a staple length between 20 mm and 150 mm, more preferably between 30 mm and 90 mm, and in particular between 40 mm and 70 mm.

The fiber titer of the fibers contained in the fiber layer, in particular of the matrix fibers and/or binding fibers, is preferably in the range of 0.9 dtex to 100 dtex (g/10,000 m). More preferably, the fiber titer is between 1.5 dtex and 30 dtex, in particular between 3 dtex and 11 dtex.

The fiber layer preferably has an average thickness, determined microscopically, of at least 1.5 mm, for example from 1.5 mm to 10 mm, more preferably of at least 2 mm, for example from 2 mm to 10 mm, and/or from 4 mm to 10 mm and/or from 2 mm to 5 mm and/or from 5 mm to 8 mm.

The basis weight of the fiber layer is preferably 50 g/m$^2$ to 400 g/m$^2$, more preferably 50 g/m$^2$ to 350 g/m$^2$, more preferably 50 g/m$^2$ to 300 g/m$^2$, more preferably 50 g/m$^2$ to 250 g/m$^2$, in particular 50 g/m$^2$ to 200 g/m$^2$.

A wide variety of foams, in particular polymer foams, can be used as the foam layer. The foam layer is preferably based on polyurethane foam, for example polyether polyurethane or polyester polyurethane foam, polyether ester polyurethane foam, polyvinyl acetate foam, polyvinyl alcohol foam, or on mixtures of these foams. The term "based on" means more than 50 wt. %, more preferably more than 70 wt. %, in particular more than 90 wt. %, in relation to the polymer portion of the foam layer.

Particularly preferably, the foam layer contains a hydrophilic polymer foam, i.e., a foam having an absorbency of at least 4 g/g, for example from 4 g/g to 50 g/g, preferably from 4 g/g to 30 g/g and more preferably from 4 g/g to 25 g/g in a proportion of more than 50 wt. %, more preferably more than 70 wt. %, in particular more than 90 wt. %, in relation to the polymer portion of the foam layer. A polymer foam made of hydrophilic polymers, preferably hydrophilic polyurethanes, in particular hydrophilic polyurethanes as described in WO2018/007093, is also preferred. A hydrophilic polymer foam allows rapid absorption of viscous wound components. Furthermore, it allows maceration of the necroses if previously impregnated with wound irrigation solution and applied to the wound. Very particular preference is given to a polyurethane foam as it combines a high degree of hydrophilic properties with good elasticity and retention. Good retention is advantageous in that removed wound components are securely enclosed so that re-contamination of the wound and its surrounding area can be prevented.

In a particularly preferred embodiment, the foam layer is open-celled. The term "open-celled" means that the majority of pores are connected to one another by pore openings. The advantage of this is that absorbed wound components can be absorbed well in the structure and distributed homogeneously.

In a further preferred embodiment, the foam layer has at least one open-celled surface. The term "open-celled surface" means that the percentage of the area of opened pores to the total surface area of the foam layer is at least 50%, for example 50% to 98%, more preferably at least 60%, for example 60% to 98%, in particular at least 70%, for example 70% to 98%. The advantage of such an open-celled foam layer is that it has a slightly abrasive character, which allows coatings to be gently detached and which can, at the same time, retain detached wound components in the structure well so that contamination of the wound is prevented.

In a further embodiment, the foam layer has a reticulated foam. With reticulated foams, the open-cell structure is produced by tearing open the pore walls by means of a gas explosion in the foam pores.

The basis weight of the foam layer is preferably 50 g/m$^2$ to 600 g/m$^2$, more preferably 80 g/m$^2$ to 500 g/m$^2$, more preferably 100 g/m$^2$ to 400 g/m$^2$, more preferably 120 g/m$^2$ to 350 g/m$^2$, in particular 120 g/m$^2$ to 250 g/m$^2$.

The average thickness of the foam layer is preferably 1 mm to 15 mm, particularly preferably 2 mm to 10 mm, and particularly preferably 3 mm to 8 mm.

The average pore size of the foam layer is at least 0.2 mm, for example 0.2 mm to 3 mm, more preferably at least 0.25 mm, for example 0.25 mm to 2.5 mm, in particular at least 0.3 mm, for example 0.3 mm to 2.2 mm.

In a further preferred embodiment, the average density of the foam layer is at least 50 kg/m$^3$, preferably from 70 kg/m$^3$ to 150 kg/m$^3$, and in particular from 90 kg/m$^3$ to 150 kg/m$^3$.

In a preferred embodiment, the composite material has an absorbency of at least 4 g/g, for example from 4 g/g to 50 g/g, preferably from 4 g/g to 30 g/g, and more preferably from 6 g/g to 25 g/g.

The basis weight of the composite material is preferably 100 g/m$^2$ to 1000 g/m$^2$, more preferably 200 g/m$^2$ to 900 g/m$^2$, more preferably 200 g/m$^2$ to 600 g/m$^2$, more preferably 200 g/m$^2$ to 500 g/m$^2$, in particular 250 g/m$^2$ to 450 g/m$^2$.

In a preferred embodiment, the composite material has a hydrophilic foam layer in combination with a hydrophobic fiber layer. A hydrophilic foam layer means a foam layer that has an absorbency of at least 4 g/g, for example from 4 g/g to 50 g/g, preferably from 4 g/g to 30 g/g, and more preferably from 4 g/g to 25 g/g. Also preferred is a foam layer consisting of a polymer foam that contains hydrophilic polymers, preferably hydrophilic polyurethanes, in particular hydrophilic polyurethanes as described in WO2018/007093, preferably in a proportion of at least 50 wt. %, more preferably at least 70 wt. %, in particular at least 90 wt. %, in relation to the total weight of the foam layer.

In a particularly preferred embodiment, the composite material has a hydrophilic foam layer in combination with a hydrophobic fiber layer, wherein hydrophobic fibers of the fiber layer penetrate the hydrophilic foam layer and protrude at least partially from the side of the foam layer facing away from the fiber layer. In this embodiment, it is advantageous that a bifunctional surface is provided on the foam layer which, due to the hydrophilic character of the foam layer, allows rapid absorption of viscous wound components and at the same time enables the adsorption of bacteria and other hydrophobic components due to the comparatively high specific surface area of the protruding fibers.

A hydrophobic fiber layer is understood to mean a fiber layer that contains hydrophobic fibers, i.e., fibers made of polymers whose surface energy is less than 50 mJ/m$^2$, preferably in a proportion of at least 50 wt. %, more preferably at least 70 wt. %, in particular at least 90 wt. %, in relation to the total weight of the fiber layer. Particularly suitable hydrophobic fibers are polyester and/or polyolefin fibers.

The wound cleaning product is preferably sterile when used for wound cleaning.

A further subject matter disclosed herein relates to the production of a wound cleaning product, comprising the following steps: arranging an at least partially thermally solidified fiber layer on a foam layer; and needling the foam layer and the fiber layer in such a way that a composite material is formed in which fibers of the fiber layer have penetrated into the foam layer and form capillary channels that extend from the fiber layer into the foam layer.

A further subject matter disclosed herein relates to an alternative production of a wound cleaning product, comprising the following steps: arranging a fiber layer on a foam layer; needling the foam layer and the fiber layer in such a way that a composite material is formed in which fibers of the fiber layer have penetrated into the foam layer and form capillary channels that extend from the fiber layer into the foam layer; and thermally solidifying the composite material.

Measuring Methods:

Determination of open-cell surface: The open-cell structure of the surface is determined by taking a light-microscopy image (e.g., interference microscope light source green) of the surface of the foam layer on an area of 1 cm×1 cm and by subsequent optical evaluation thereof. The percentage of the area of opened pores to the total surface area of the foam layer is determined.

Pore diameter of the pores in the foam layer: The pore diameter is determined by optical evaluation of light-microscopy images by applying an outer circle. The pore diameter corresponds to the diameter of the outer circle. The average is formed by evaluating at least 10 pores.

Absorbency: For absorption measurements, a test solution as described in BS EN 13726-1:2002 is used. A 100 cm² large sample is first weighed (W1), then placed in the test solution, and left there for at least ten minutes. Afterwards, the sample is carefully grasped at one corner without squeezing the sample and is allowed to drip for two minutes. The weight is then determined again (W2). Now, the absorbency is calculated as absorption [g] per [g] by dividing the difference in the magnitude of W2 and W1 by the initial weight W1. Density of the foam layer: The density is determined by cutting out a sample, weighing it, and determining the thickness. The volume is then calculated by multiplying the thickness by the area of the sample; and finally, the weight is divided by the volume.

Thickness of the foam layer: The thickness of the foam layer is determined microscopically prior to needling to the fiber layer.

FIG. 1 shows the cross-section of a CT image of a composite material 1 having a foam layer 2 and a fiber layer 3 arranged thereon. Foam layer 2 and fiber layer 3 are connected to one another by needling so that fibers of the fiber layer 3 have penetrated into the foam layer 2 and form capillary channels 4 therein. It can be seen that the capillary channels 4 extend from the fiber layer 3 into the foam layer 2.

Figure 2:
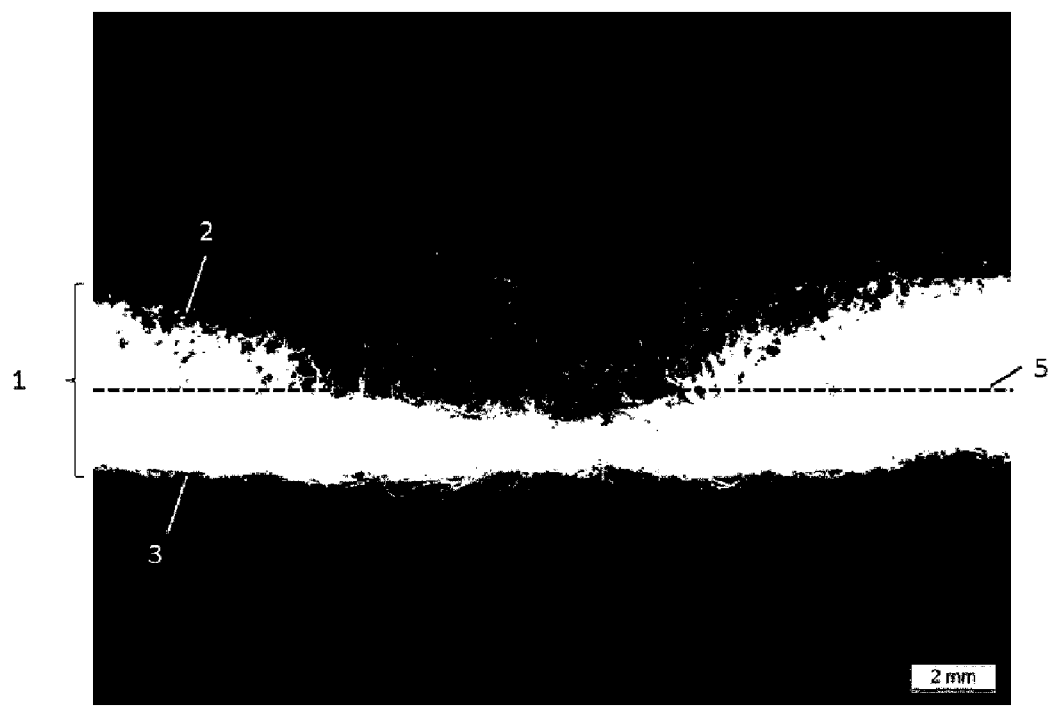
FIG. 2 shows the cross-section of a light-microscopy image of a composite material after wound cleaning, according to an embodiment.

FIG. 2 shows the cross-section of a light-microscopy image of a composite material 1 after wound cleaning with the foam side. In the figure, the interface of foam layer 2 and fiber layer 3 is illustrated as a boundary line 5. It can clearly be seen how wound components are absorbed deeply in the foam layer 2 and pass the boundary line 5, i.e., have penetrated into the fiber layer 3.

Figure 3:
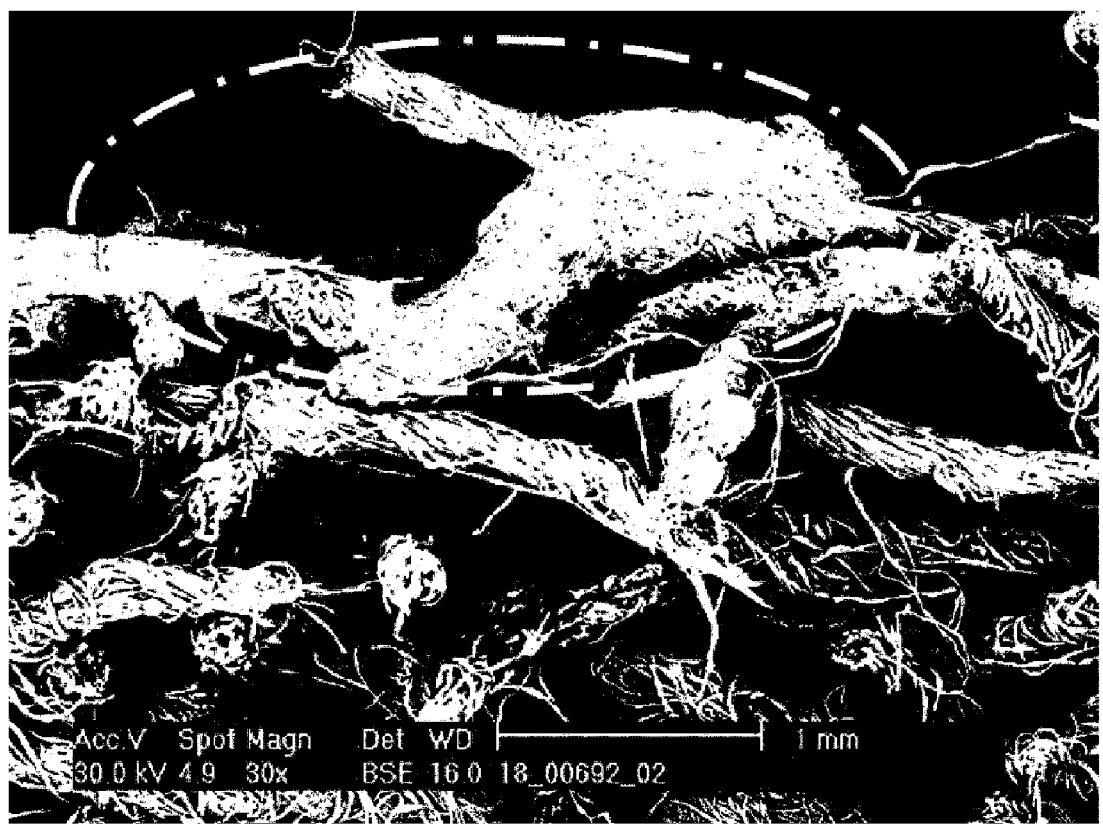
FIG. 3 shows the cross-section of an SEM image of a cotton gauze after wound cleaning.

FIG. 3 shows the cross-section of an SEM image of a cotton gauze after wound cleaning. It can clearly be seen how the wound components are retained only on the surface of the cotton gauze (area within the dot-dash line).

Figure 4:
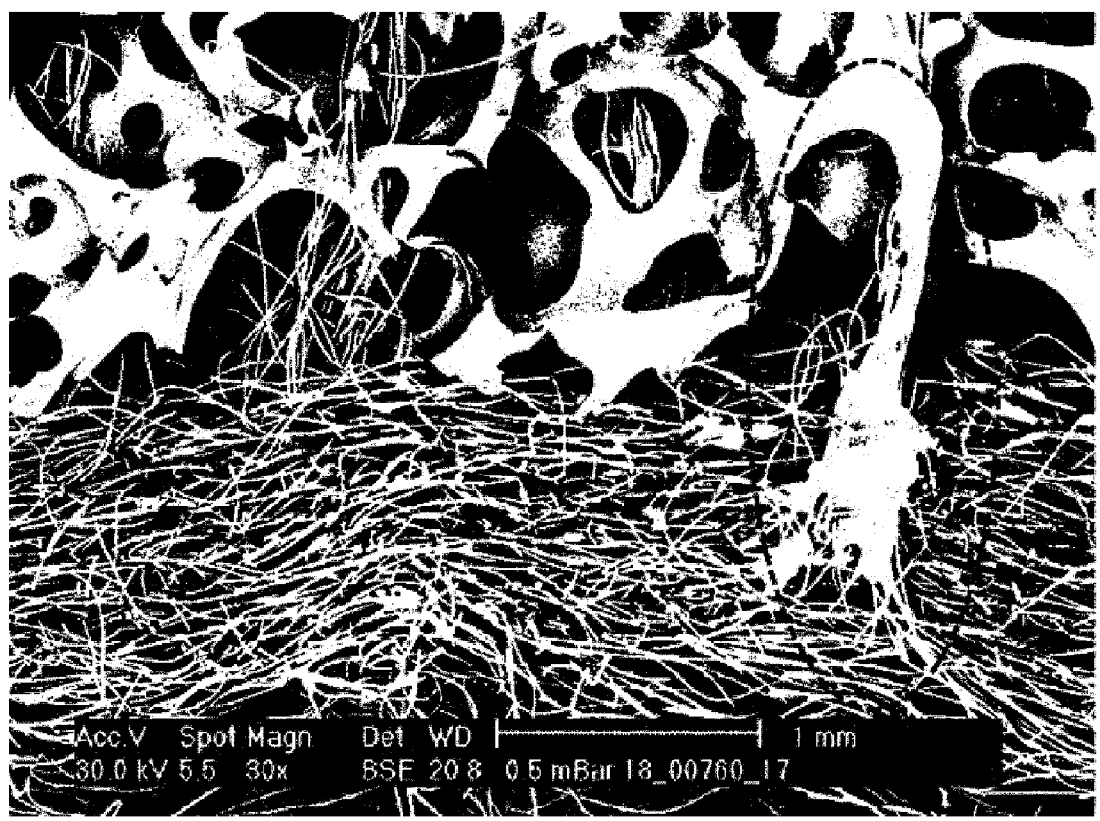
FIG. 4 shows the cross-section of an SEM image of a wound cleaning material after wound cleaning, according to an embodiment.

FIG. 4 shows the cross-section of an SEM image of a wound cleaning material after wound cleaning. It can clearly be seen how wound exudate is conducted along the capillary channels formed by fibers from the foam layer into the fiber layer (marked within dotted line).

Figure 5:
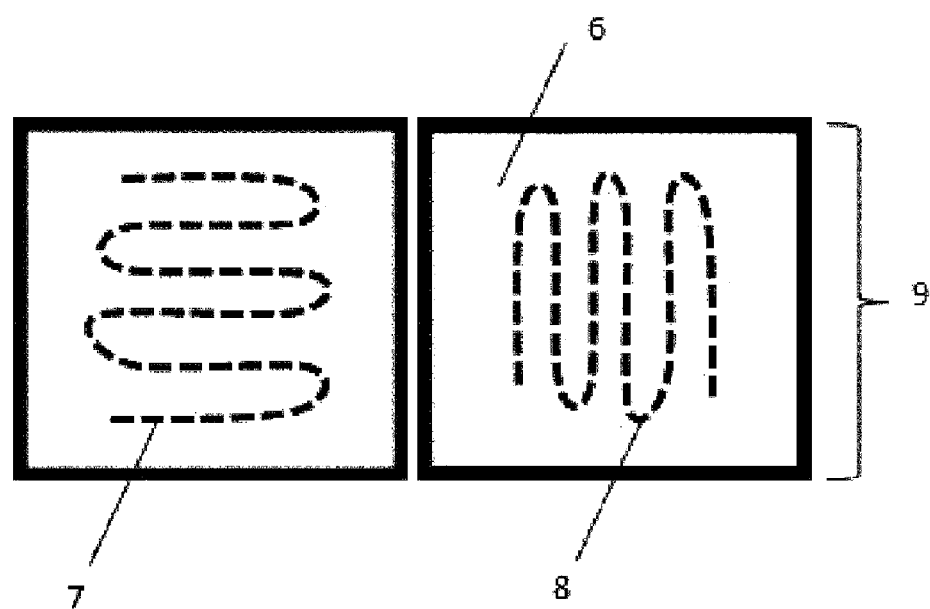
FIG. 5 shows the defined movement of a wiping cycle for cleaning a test wound on porcine skin.

FIG. 5 shows the defined movement of a wiping cycle for cleaning a test wound on porcine skin. The wound surface 6 is cleaned with slight pressure (to simulate gentle cleaning) and in a defined horizontal 7 and vertical 8 movement, which result in a wiping cycle 9.

Figure 6:
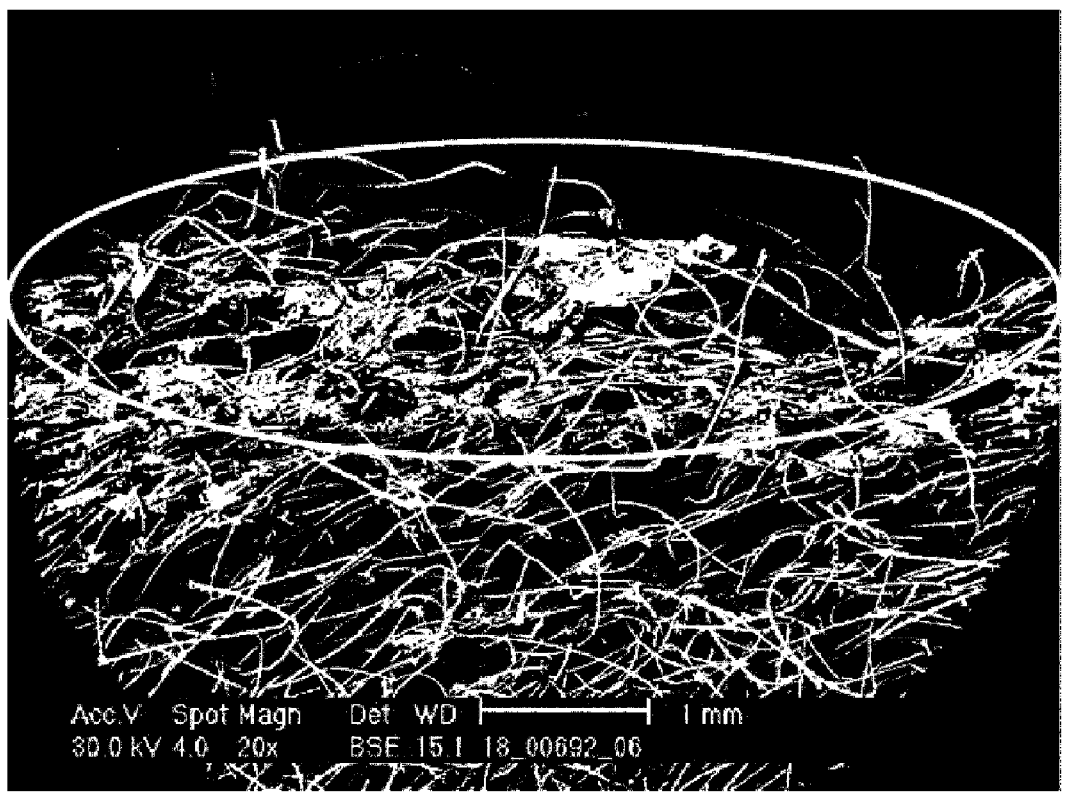
FIG. 6 shows the cross-section of an SEM image of the product Debrisoft® after wound cleaning.

FIG. 6 shows the cross-section of an SEM image of the product Debrisoft® after wound cleaning. It can clearly be seen how the wound components are retained only on the surface (area within the oval).

EXAMPLE 1: PRODUCTION OF A FOAM LAYER

A water phase is prepared for foam production by dissolving/dispersing the surfactant Pluronic F87 at a concentration of 0.5 wt. %. At the same time, a Teflon mold of sufficient depth is lined with casting paper in order to produce a foam of 7 mm thickness. The prepolymer Hypol 2001 is added to the water phase at a concentration of 40 wt. % and mixed at room temperature with a dispersion disk (1,600 rpm). The obtained mixture is immediately poured into the casting mold. It is foamed in air and cured for 10 minutes. Thereafter, the casting paper is removed, and drying takes place at a temperature of 150° C. for 3 hours.

EXAMPLE 2: PRODUCTION OF A THERMALLY SOLIDIFIED FIBER LAYER

Staple fibers are used to produce the thermally solidified fiber layer: 70 wt. % polyester fibers (Grisuten® by Markische Faser GmbH) having a fiber titer of 1.7 dtex and a fiber length of 60 mm and 30 wt. % of a polyethylene terephthalate/polyethylene core-sheath binding fiber (Trevira® 256 by Trevira GmbH) having a fiber titer of 3 dtex and a fiber length of 50 mm. These staple fibers are placed into a fiber layer by means of a carding machine according to methods known to the person skilled in the art. The basis weight of the fiber layer is 150 g/m². The fiber layer is then thermoset in a hot air furnace at 150° C. and a velocity of 2 m/min.

EXAMPLE 3: PRODUCTION OF A WOUND CLEANING PRODUCT BY MECHANICALLY NEEDLING THE FIBER LAYER AND FOAM LAYER

In order to produce the wound cleaning product according to an embodiment, an open-pore foam layer from Example 1 and a thermally solidified fiber layer from Example 2 are provided. In a needling process, the nonwoven layer is needled against the foam layer with a puncture density of 100/cm² and a puncture depth of 10 mm. In this case, the surface of the nonwoven layer which was facing away from the belt side in the furnace is located on the side facing away from the foam layer surface. Foam layer and fiber layer are connected to one another by the needling process. In this way, both a mechanically stable composite and a slightly fibrous surface are created on the foam. In addition, the fibers of the fiber layer penetrate the foam layer, form capillary channels in the foam layer, and protrude at least partially from the side of the foam layer facing away from the fiber layer. The composite material obtained has a higher abrasiveness on the foam layer than on the fiber layer. Due to the fibers protruding from the foam layer, the foam layer has a more pleasant feel than the pure foam layer. In order to produce a wound cleaning product, the composite material is tailored. No significant loss of fibers occurs in doing so.

EXAMPLE 4: DETERMINATION OF THE MECHANICAL STABILITY OF THE COMPOSITE MATERIAL FROM EXAMPLE 3

Mechanical stability is tested as the tensile strength of the composite material according to the invention with the aid of a tensile test according to EN 29073-03 (deviations: no conditioning and pull-off speed 200 mm/min) in the longitudinal direction with a specimen size of 300×50 mm. The tensile strength in dry and wet condition were determined since wound cleaning materials are generally used when moist. In order to assess the tensile strength in wet condition, the specimens were placed in tap water for approximately 30 minutes, then slightly squeezed and allowed to drip in a suspended state for 5-10 minutes.

Table 1 shows, in comparison, the maximum tensile strength and breaking extension for an open-cell foam, the composite material according to an embodiment, and the standard cotton gauze. The composite material has a significantly higher maximum tensile strength in wet and dry condition than a pure open-cell foam. As a result of the fiber layer penetrating into the foam layer, the foam layer is mechanically reinforced and the tensile strength is increased. In the dry condition, the strength of a standard cotton pad is thereby achieved. In the wet condition, the composite material according to the invention has a lower, but sufficient, maximum tensile strength than the standard cotton gauze. In contrast, the breaking extension is significantly higher than that of the cotton gauze. As a result, the composite material is excellently suitable for wet wound cleaning since its high stretchability can prevent tearing during cleaning. Furthermore, the increased expansion offers the advantage that the composite material can better adapt to the wound bed.

TABLE 1

COMPARISON OF AVERAGE MAXIMUM TENSILE STRENGTH AND BREAKING EXTENSION FOR OPEN-CELL FOAM, A COMPOSITE MATERIAL ACCORDING TO THE INVENTION, AND STANDARD COTTON GAUZE

|  | Dry | | Wet | |
| --- | --- | --- | --- | --- |
|  | Maximum tensile strength [N] | Breaking extension [%] | Maximum tensile strength [N] | Breaking extension [%] |
| Open-cell foam layer [2.5 mm] | 22.1 | 165.8 | 10.2 | 58.9 |
| Composite material according to the invention [~4 mm] | 87.4 | 135.3 | 76.0 | 130.3 |
| Standard cotton gauze [<1 mm] | 83.3 | 5.0 | 143.7 | 8.2 |

EXAMPLE 5: DETERMINATION OF THE CLEANING PERFORMANCE OF THE WOUND CLEANING PRODUCT IN AN EX-VIVO WOUND MODEL

The composite material produced in Example 3 was tailored by stamping to a size of 10 cm×10 cm to form a wound cleaning product according to an embodiment. The cleaning performance of the wound cleaning product was evaluated on porcine skin using an ex-vivo wound model. The wound to be cleaned was prepared as follows. The porcine skin was first fixed in a frame (area for wound 10 cm×10 cm), with the inside of the skin facing up, carved in a defined manner with a scalpel in the form of a lattice pattern. The skin was then slightly burned using a blowtorch (20 seconds, average flame, distance approx. 20 cm) so as to produce an uneven wound bed as the cuts gape. Escaping fat was carefully removed with a paper towel by tapping. Then, 4 mL of egg white solution (100 g/L egg white powder (for example Body&Fit Egg White Powder dissolved in phosphate-buffered saline solution (8.0 g/L sodium chloride (NaCl), 0.2 g/L potassium chloride (KCl), 1.42 g/L disodium hydrogen phosphate ($Na_2HPO_4$) or 1.78 g/L disodium hydrogen phosphate dihydrate ($Na_2HPO_4 \cdot 2\ H_2O$), 0.27 g/L potassium dihydrogen phosphate ($KH_2PO_4$))) were applied and again burned in using a blowtorch (30 seconds, average flame, distance approx. 20 cm). The egg white solution is suitable for simulating fibrin coatings in the wound. In a final step, 2 g of artificial exudate solution (5% Blanose, 40 g/L egg white powder, 1 g/L sugar, artificial blood (150 drops to 300 mL, 2 g/L sunflower oil, 3.7 g/L sodium carbonate, 3 g/L quartz sand, all dissolved in PBS) are applied to the wound using a wooden spatula and burned in again until a black crust (partially) forms (30 seconds, average flame, distance approx. 20 cm). The simulated wound is left to rest at room temperature for 2 hours so that previously applied exudate cannot be easily removed again.

For cleaning, the wound cleaning product was moistened on the foam side (10 cm×10 cm) with 5 sprays of water and placed on the wound for one minute, with the foam side facing the wound surface. The wound surface was then cleaned with slight pressure (to simulate gentle cleaning) and in a defined horizontal and vertical movement, which result in a wiping cycle (see FIG. 5). Cleaning is carried out for 3 minutes with 11 wiping cycles.

The cleaning performance was evaluated via image analysis of the burned (black) areas before and after wound cleaning. The prepared porcine skins were recorded with a single-lens reflex camera (Canon D70) with a fixed focal length objective (60 mm) using a copystand. In doing so, care was taken that the illumination and the distance (resulting magnification) between the object and the objective were the same for all images taken. A metal frame for smoothing the porcine skins was applied during the tests. The black areas in the image were located and marked in green by specifying a threshold and using a 15×15 pixel median filter. An upper limit of 80 in the histogram was selected for all images. This and the unchanging recording setup ensure that the results of all samples are comparable. As a final step, the area of the image to be reasonably evaluated was limited (ROI). Due to the calibration of the images during the recording, it was subsequently possible to specify the marked areas as area fractions in μm.

TABLE 2

COMPARISON OF THE CLEANING PERFORMANCE OF COTTON GAUZE, DEBRISOFT ®, AND A WOUND CLEANING PRODUCT ACCORDING TO THE INVENTION

|  | Surface area before cleaning [mm$^2$] | Surface area after cleaning [mm$^2$] | Cleaning performance in [%] |
|---|---|---|---|
| Cotton gauze | 629.0 | 286.0 | 54.5 |
| Cotton gauze | 1491.0 | 1010.0 | 32.3 |
| Debrisoft ® | 3162.0 | 1276.0 | 59.6 |
| Debrisoft ® | 3374.0 | 1289.0 | 61.7 |
| Wound cleaning product according to the invention | 2924.0 | 922.0 | 68.5 |
| Wound cleaning product according to the invention | 59.0 | 14.0 | 76.3 |

EXAMPLE 6 DETERMINATION OF THE ABSORPTION OF WOUND COMPONENTS BY THE WOUND CLEANING PRODUCT ACCORDING TO THE INVENTION FROM EXAMPLE 5

Light-microscopy and SEM images were made in order to determine the absorption of wound components in the wound cleaning product. It can clearly be seen (FIG. 2) that wound components are transported beyond the boundary of the foam layer and into the fiber layer. In contrast, absorption in cotton gauze (FIG. 3: area within the dot-dash oval) and Debrisoft (FIG. 6: area within the oval) takes place only on the surface or in the upper part of the structure. It can also be seen (FIG. 3: dashed area) that the capillary channels allow a transport of exudate across layers and its enclosure in the entire wound cleaning product.

The wound cleaning product is tested according to BS EN 13726-1:2002 with regard to its absorbency in comparison to cotton gauze and the product Debrisoft®. It has been found to show an increased absorption of the aqueous test solution in comparison to standard cotton gauze and to the product Debrisoft® (cf. Table 3). This is advantageous in that more wound components and liquids, such as irrigation solutions used in support of wound cleaning and/or wound exudate, can be absorbed during one wound cleaning application.

TABLE 3

COMPARISON OF THE ABSORPTION OF COTTON GAUZE, DEBRISOFT ®, AND A WOUND CLEANING PRODUCT ACCORDING TO THE INVENTION

|  | Absorption [g/g] |
|---|---|
| Cotton gauze | 5.2 |
| Debrisoft ® | 5.9 |
| Wound cleaning product according to the invention | 6.5 |

While subject matter of the present disclosure has been illustrated and described in detail in the drawings and foregoing description, such illustration and description are to be considered illustrative or exemplary and not restrictive. Any statement made herein characterizing the embodiments are also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A wound cleaning product comprising a composite material having a foam layer and a fiber layer arranged on a surface of the foam layer, wherein the fiber layer is at least partially thermally solidified, and the foam layer and the fiber layer are connected to one another by needling such that fibers of the fiber layer have penetrated into the foam layer and form capillary channels that extend from the fiber layer into the foam layer,
    wherein the composite material has a maximum tensile strength/expansion measured according to EN 29073-03 (wet) of more than 40%.

2. The wound cleaning product according to claim 1, wherein the fibers of the fiber layer penetrate the foam layer and protrude at least partially from a second surface of the foam layer facing away from the fiber layer.

3. The wound cleaning product according to claim 1, wherein the fiber layer comprises synthetic fibers.

4. The wound cleaning product according to claim 1, wherein the fiber layer comprises matrix fibers and a binder.

5. The wound cleaning product according to claim 1, wherein the fiber layer comprises hydrophobic fibers.

6. The wound cleaning product according to claim 1, wherein the fibers contained in the fiber layer are staple fibers of a staple length between 20 mm and 150 mm.

7. The wound cleaning product according to claim 1, wherein the foam layer comprises a hydrophilic polymer foam in a proportion of more than 50 wt. % in relation to a polymer proportion of the foam layer.

8. The wound cleaning product according to claim 1, wherein the foam layer has an open-cell structure.

9. The wound cleaning product according to claim 1, wherein the foam layer has at least one open-cell surface.

10. The wound cleaning product according to claim 1, wherein the composite material has a hydrophilic foam layer in combination with a hydrophobic fiber layer.

11. The wound cleaning product according to claim 10, wherein hydrophobic fibers of the hydrophobic fiber layer penetrate the hydrophilic foam layer and protrude at least partially from a second surface of the foam layer facing away from the fiber layer.

12. The wound cleaning product according to claim 1, wherein the wound cleaning product is sterile.

13. A method for producing a wound cleaning product, the method comprising:

arranging an at least partially thermally solidified fiber layer on a foam layer; and needling the foam layer and the fiber layer to form a composite material such that fibers of the fiber layer have penetrated into the foam layer and form capillary channels that extend from the fiber layer into the foam layer, wherein the composite material has a maximum tensile strength/expansion measured according to EN 29073-03 (wet) of more than 40%.

14. A method for producing a wound cleaning product, the method comprising:

arranging a fiber layer on a foam layer;

needling the foam layer and the fiber layer to form a composite material such that fibers of the fiber layer have penetrated into the foam layer and form capillary channels that extend from the fiber layer into the foam layer; and thermally solidifying the composite material, wherein the composite material has a maximum tensile strength/expansion measured according to EN 29073-03 (wet) of more than 40%.

* * * * *